(12) United States Patent
Wang et al.

(10) Patent No.: US 9,451,879 B2
(45) Date of Patent: Sep. 27, 2016

(54) OPTICAL APPARATUS AND OPERATING METHOD THEREOF

(71) Applicant: Crystalvue Medical Corporation, Taoyuan (TW)

(72) Inventors: William Wang, Taoyuan (TW); Chung-Ping Chuang, Taoyuan (TW); Meng-Shin Yen, Taipei (TW); Chung-Cheng Chou, Taoyuan County (TW)

(73) Assignee: CRYSTALVUE MEDICAL CORPORATION, Taoyuan (TW)

( * ) Notice: Subject to any disclaimer, the term of this patent is extended or adjusted under 35 U.S.C. 154(b) by 314 days.

(21) Appl. No.: 14/263,428

(22) Filed: Apr. 28, 2014

(65) Prior Publication Data

US 2014/0320811 A1  Oct. 30, 2014

(30) Foreign Application Priority Data

Apr. 30, 2013  (TW) .............................. 102115466 A

(51) Int. Cl.
| | |
|---|---|
| *A61B 3/14* | (2006.01) |
| *A61B 3/00* | (2006.01) |
| *A61B 3/10* | (2006.01) |
| *A61B 3/12* | (2006.01) |
| *A61B 3/16* | (2006.01) |

(52) U.S. Cl.
CPC ................. *A61B 3/14* (2013.01); *A61B 3/102* (2013.01); *A61B 3/12* (2013.01); *A61B 3/16* (2013.01)

(58) Field of Classification Search
USPC ................................. 351/206, 208, 209, 246
See application file for complete search history.

(56) References Cited

U.S. PATENT DOCUMENTS

| | | | |
|---|---|---|---|
| 2007/0279588 A1* | 12/2007 | Hammoud | A61B 3/113 351/206 |
| 2015/0235084 A1* | 8/2015 | Cho | A61B 3/113 345/581 |

* cited by examiner

*Primary Examiner* — Jack Dinh
(74) *Attorney, Agent, or Firm* — Muncy, Geissler, Olds & Lowe, P.C.

(57) ABSTRACT

An optical apparatus applied to ophthalmology detection is disclosed. The optical apparatus includes an image capturing unit, a data comparing unit, a detection unit, a location determining unit, and a data output unit. The image capturing unit captures images of different portions of a face of a person to be tested to obtain a plurality of face images. The data comparing unit compares the plurality of face images with a built-in database. The detection unit detects on an eye of the person to be tested. The location determining unit automatically determines whether the eye detected by the detection unit is left-eye or right-eye. The data output unit selectively outputs a detection result of the detection unit, a comparing result of the data comparing unit, and/or a determining result of the location determining unit.

14 Claims, 3 Drawing Sheets

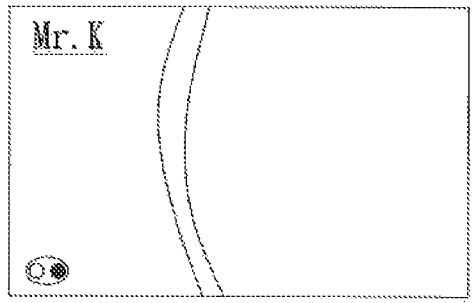
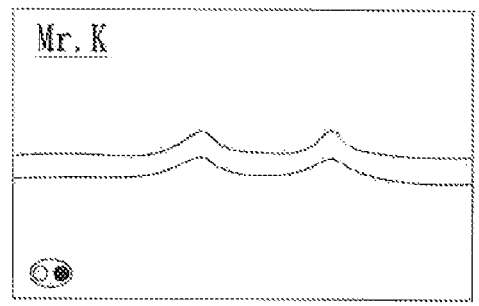
FIG. 3A  FIG. 3B
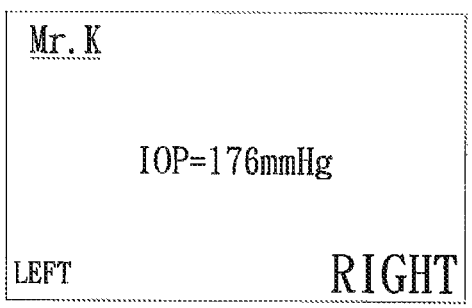
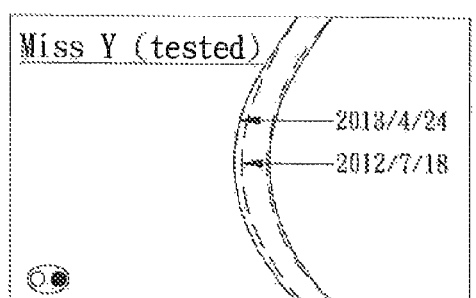
FIG. 3C  FIG. 3D

OPTICAL APPARATUS AND OPERATING METHOD THEREOF

BACKGROUND OF THE INVENTION

1. Field of the Invention

The invention relates to optical detection, in particular, to an optical apparatus and operating method thereof suitable for ophthalmology detection.

2. Description of the Prior Art

In recent years, with the continuous development of the optical detection technology, the optical image scanning technology provides a non-invasive way to observe the structure and composition of the object to be detected. It can be widely used in human body function detection and medical diagnosis.

Because human eye and surrounding tissue are mostly translucent material, the optical detection technology is widely applied in ophthalmology detection apparatus, such as an optometry machine, a tonometer, a fundus camera, a corneal thickness meter, and an optical coherence tomography (OCT). The detection results obtained by the above-mentioned ophthalmology detection apparatus are usually stored in digital type to facilitate the follow-up procedures such as access, copy, or after-treatment.

For an operator, how to rapidly analyze and process the detection data obtained by the ophthalmology detection apparatus is very important. Therefore, the invention provides an optical apparatus and operating method thereof suitable for ophthalmology detection to solve the above-mentioned problems.

SUMMARY OF THE INVENTION

A first embodiment of the invention is an optical apparatus applied to ophthalmology detection. In this embodiment, the optical apparatus includes an image capturing unit, a data comparing unit, a detection unit, a location determining unit, and a data output unit. The image capturing unit captures images of different portions of a face of a person to be tested to obtain a plurality of face images. The data comparing unit compares the plurality of face images with a built-in database. The detection unit detects on an eye of the person to be tested. The location determining unit automatically determines whether the eye detected by the detection unit is left-eye or right-eye. The data output unit selectively outputs a detection result of the detection unit, a comparing result of the data comparing unit, and/or a determining result of the location determining unit.

In an embodiment, the data comparing unit includes the plurality of face images with the built-in database to determine whether the person to be tested is a new tester.

In an embodiment, the location determining unit includes a proximity sensor. When the detection unit approaches the eye of the person to be tested, the proximity sensor automatically senses whether the detection unit moves left or right to determine the eye detected by the detection unit is the left-eye or the right-eye.

In an embodiment, the proximity sensor is a capacitive-resistive type, a photoelectric emitting-receiving type, a flux induction type, an ultrasound type, or an optical scale type.

In an embodiment, the optical apparatus is hand-held, and the location determining unit includes a motion sensor. When the optical apparatus is held by a hand to approach the eye of the person to be tested, the motion sensor automatically senses whether the hand moves left or right to determine the eye detected by the detection unit is the left-eye or the right-eye In an embodiment, the detection unit detects on the eye of the person to be tested via an optometry technology, a fundus photography technology, an optical coherence tomography (OCT) technology, an intraocular pressure (IOP) detection technology, a corneal thickness detection technology, or a corneal curvature detection technology.

In an embodiment, the data output unit marks the detection result of the detection unit, the comparing result of the data comparing unit, and/or the determining result of the location determining unit by displaying graphic data or text data.

A second embodiment of the invention is an optical apparatus operating method. In this embodiment, the optical apparatus operating method is applied to ophthalmology detection. The optical apparatus includes an image capturing unit, a data comparing unit, a detection unit, a location determining unit, and a data output unit. The method includes steps of: (a) the image capturing unit capturing images of different portions of a face of a person to be tested to obtain a plurality of face images; (b) the data comparing unit comparing the plurality of face images with a built-in database; (c) the detection unit detecting on an eye of the person to be tested; (d) the location determining unit automatically determining whether the eye detected by the detection unit is a left-eye or a right-eye; and (e) the data output unit selectively outputting a detection result of the detection unit, a comparing result of the data comparing unit, and/or a determining result of the location determining unit.

Compared to the prior arts, the optical apparatus and the operating method thereof have many advantages as follows:

(1) capable of automatically identifying the person to be tested;

(2) capable of cooperating with other optical detection apparatus with different functions, such as an optometry machine, a tonometer, a fundus camera, a corneal thickness meter, and an optical coherence tomography (OCT);

(3) capable of rapidly determining whether the eye detection data is related to left-eye or right-eye;

(4) capable of providing the tracking and comparing result of the detection data.

The advantage and spirit of the invention may be understood by the following detailed descriptions together with the appended drawings.

BRIEF DESCRIPTION OF THE APPENDED DRAWINGS

FIG. 3A and FIG. 3B illustrate the data output unit of the optical apparatus displaying the detection results of corneal thickness, corneal curvature, and retinal optical coherence tomography (OCT) respectively.

FIG. 3C illustrates the data output unit of the optical apparatus displaying the intraocular pressure (IOP) detection result of the eyes of the person to be tested.

FIG. 3D illustrates the data output unit of the optical apparatus displaying the comparing result after comparing the detection results of the eyes of the person to be tested in different periods.

DETAILED DESCRIPTION OF THE INVENTION

An embodiment of the invention is an optical apparatus. In this embodiment, the optical apparatus can be an optical ophthalmology detection apparatus, but not limited to this. It should be noticed that the optical apparatus of the invention can not only automatically identify the person to be tested, but also cooperate with other optical detection apparatus with different functions, such as an optometry machine, a tonometer, a fundus camera, a corneal thickness meter, and an optical coherence tomography (OCT). In addition, the optical apparatus can also rapidly determine whether the eye detection data is related to left-eye or right-eye and provide tracking and comparing result of the detection data. Therefore, the operator can use the optical apparatus of the invention to analyze and process the detection data rapidly.

Figure 1:
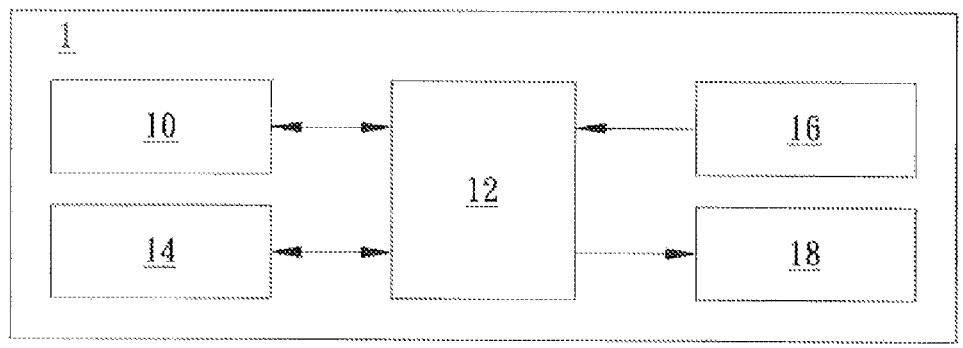
FIG. 1 illustrates a function block diagram of the optical apparatus in an embodiment of the invention.
Figure 2A:
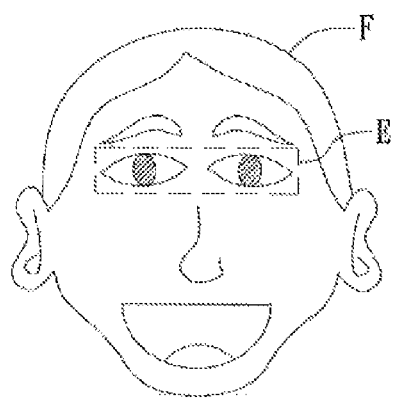
FIG. 2A illustrates a schematic figure of the face and eyes of the person to be tested under the detection of the optical apparatus.

Please refer to FIG. 1. FIG. 1 illustrates a function block diagram of the optical apparatus in this embodiment. As shown in FIG. 1, the optical apparatus 1 is used to perform an ophthalmology detection procedure on eyes E of a person to be tested (see FIG. 2A). The optical apparatus 1 includes an image capturing unit 10, a data comparing unit 12, a detection unit 14, a location determining unit 16, and a data output unit 18. Wherein, the image capturing unit 10 is coupled to the data comparing unit 12; the detection unit 14 is coupled to the data comparing unit 12; the location determining unit 16 is coupled to the data comparing unit 12; the data output unit 18 is coupled to the data comparing unit 12.

Before the optical apparatus 1 performs detection, the image capturing unit 10 will capture images of different portions of a face F of the person to be tested (see FIG. 2A) to obtain a plurality of face images. It should be noticed that the portion of the face F which is captured can be determined based on practical needs without specific limitations. For example, the image capturing unit 10 can capture the image of the entire face F or only capture the tissue of the eyes E, such as iris or retinal artery.

Then, the data comparing unit 12 compares the plurality of face images of the face F of the person to be tested with a built-in database to identify the person to be tested. For example, if the data comparing unit 12 fails to find out any default image data matching the plurality of face images, the data comparing unit 12 will determine that the person to be tested is a new tester and create a new data file for the new tester to store the plurality of face images and other related data for future comparison purposes. If the data comparing unit 12 finds out a default image data matching the plurality of face images, the data comparing unit 12 can identify the person to be tested and access the data related to the person to be tested from the data file of the person to be tested for reference.

After the identity of the person to be tested is determined, the detection unit 14 of the optical apparatus 1 will detect on the eye E (left eye or right eye) of the person to be tested. It should be noticed that the detection unit 14 can detect on the eye E of the person to be tested via an optometry technology (vision testing), a fundus photography technology (retinal plane detection), an optical coherence tomography (OCT) technology (retinal cross-section detection), an intraocular pressure (IOP) detection technology, a corneal thickness detection technology, a corneal curvature detection technology, or other ophthalmology detection technologies.

When the detection unit 14 of the optical apparatus 1 approaches the eye E of the person to be tested, the location determining unit 16 of the optical apparatus 1 will automatically determine whether the eye E detected by the detection unit 14 is the left-eye or the right-eye.

Figure 2B:
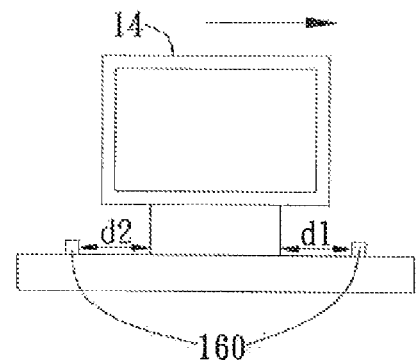
FIG. 2B and FIG. 2C illustrate schematic figures of the proximity sensor of the location determining unit automatically sensing that the detection unit moves right according to the distance variation between the proximity sensor and the detection unit.
Figure 2C:
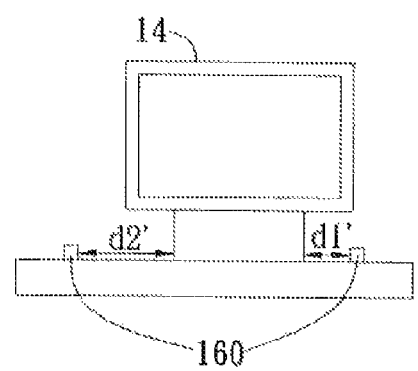

For example, the location determining unit 16 can include a proximity sensor. When the detection unit 14 approaches the eye E of the person to be tested, the proximity sensor of the location determining unit 16 will automatically sense whether the detection unit 14 moves left or right (as shown in FIG. 2B and FIG. 2C, the proximity sensor 160 of the location determining unit 16 will automatically sense that the detection unit 14 moves right according to the distance variation between the proximity sensor 160 and the detection unit 14) to determine the eye detected by the detection unit 14 is the left-eye or the right-eye. In practical applications, the proximity sensor 160 of the location determining unit 16 can be a capacitive-resistive type, a photoelectric emitting-receiving type, a flux induction type, an ultrasound type, or an optical scale type.

In another embodiment, if the optical apparatus 1 is hand-held, the location determining unit 16 can include a motion sensor. When the optical apparatus 1 is held by a hand of an operator to approach the eye E of the person to be tested, the motion sensor of the location determining unit 16 will automatically sense whether the hand of the operator moves left or right to determine the eye E detected by the detection unit 14 is the left-eye or the right-eye.

From above, it can be found that since the optical apparatus 1 determines the identity of the person to be tested according to the comparing result of the data comparing unit 12, obtains the detection result of the eye E of the person to be tested from the detection unit 14, and uses the location determining unit 16 to determine the eye E detected by the detection unit 14 is the left-eye or the right-eye, the data output unit 18 of the optical apparatus 1 can selectively output the detection result of the detection unit 14, the comparing result of the data comparing unit 12, and/or the determining result of the location determining unit 16 according to different purposes or needs.

For example, please refer to FIG. 3A and FIG. 3B. FIG. 3A and FIG. 3B illustrate the data output unit 18 of the optical apparatus 1 displaying the detection results of corneal thickness, corneal curvature, and retinal optical coherence tomography (OCT) of the eye E respectively. As shown in FIG. 3A and FIG. 3B, a graphic data (including a light part and a dark part) is used to mark the lower left corner of FIG. 3A and the lower left corner FIG. 3B that the right eye of the person to be tested is detected and a text data is used to mark the upper left corner of FIG. 3A and the lower left corner FIG. 3B that the identity of the person to be tested is Mr. K who has been tested before.

Please also refer to FIG. 3C. FIG. 3C illustrates the data output unit 18 of the optical apparatus 1 displaying the intraocular pressure (IOP) detection result of the eyes E of the person to be tested. As shown in FIG. 3C, a smaller text "LEFT" and a larger text "RIGHT" are marked at the lower left corner and the lower right corner of FIG. 3C respectively to show that the right eye of the person to be tested is detected. And, the number is used to mark the intraocular pressure (IOP) value of the right eye of the person to be tested. The upper left corner of FIG. 3C is marked by the text data to show the identity of the person to be tested is Mr. K who has been tested before.

In addition, if the identity of the person to be tested is someone who has been tested before, the data comparing unit 12 of the optical apparatus 1 can further compare the detection results of the eyes of the person to be tested in different periods and then the data output unit 18 of the optical apparatus I will display the comparing result. For example, as shown in FIG. 3D, the solid line represents the current corneal curvature and thickness detection result of the eyes of the person to be tested (date: 2013 April 24) and the dotted line represents the previous corneal curvature and thickness detection result of the eyes of the person to be tested (date: 2012 July 18). A graphic data (including a light part and a dark part) is used to mark the lower left corner of FIG. 3D that the right eye of the person to be tested is detected. The upper left corner of FIG. 3D is marked by the text data to show the identity of the person to be tested is Miss Y who has been tested before.

Figure 4:
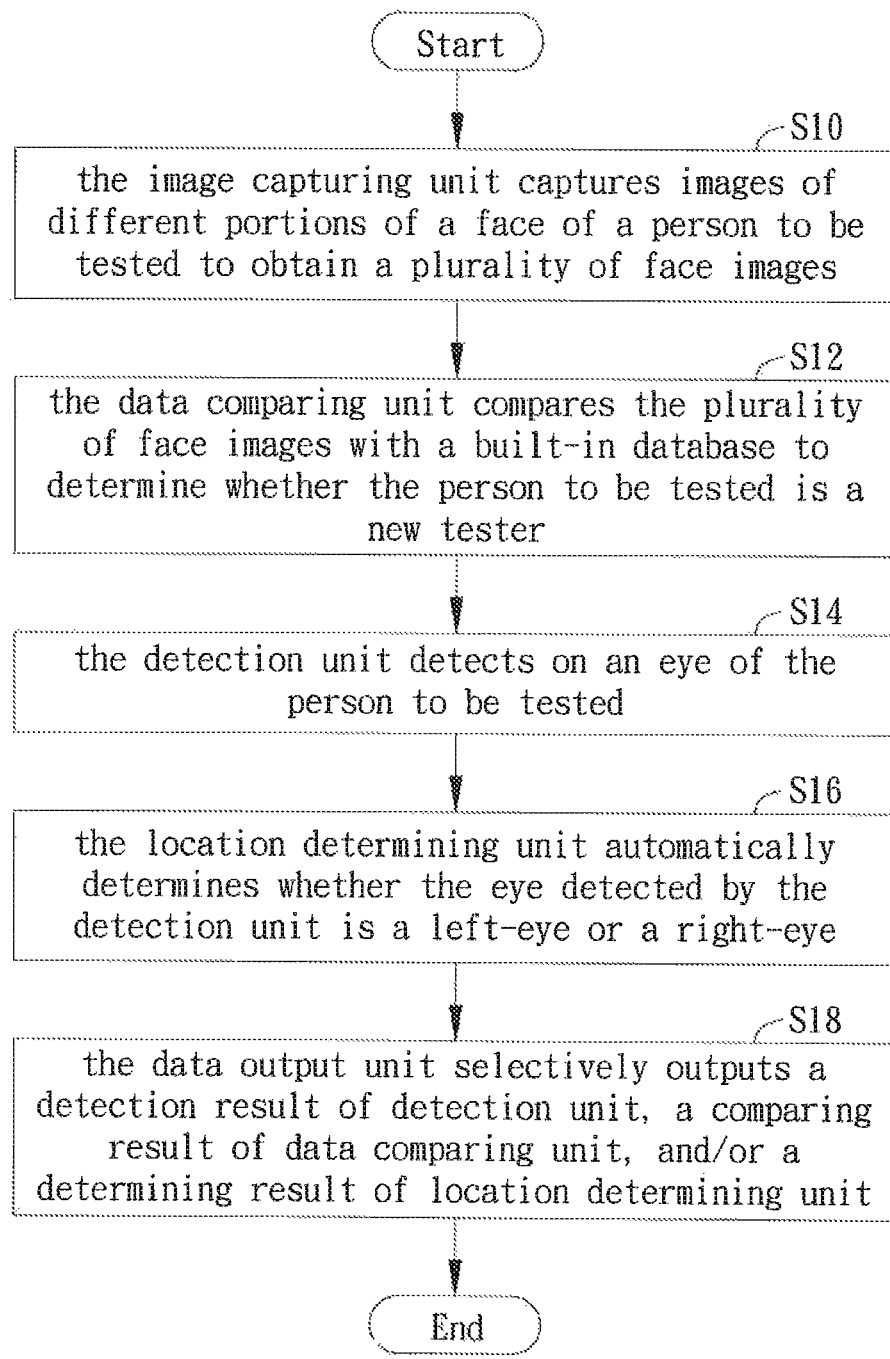
FIG. 4 illustrates a flowchart of the optical apparatus operating method in another embodiment of the invention.

Another embodiment of the invention is an optical apparatus operating method. In this embodiment, the optical apparatus operating method is applied to ophthalmology detection. The optical apparatus includes an image capturing unit, a data comparing unit, a detection unit, a location determining unit, and a data output unit. Please refer to FIG. 4. FIG. 4 illustrates a flowchart of the optical apparatus operating method in this embodiment.

As shown in FIG. 4, at first, in step S10, the image capturing unit captures images of different portions of a face of a person to be tested to obtain a plurality of face images. Then, in step S12, the data comparing unit compares the plurality of face images with a built-in database to determine whether the person to be tested is a new tester.

Then, in step S14, the detection unit detects on an eye of the person to be tested. In fact, the detection unit can detect on the eye of the person to be tested via an optometry technology, a fundus photography technology, an optical coherence tomography (OCT) technology, an intraocular pressure (IOP) detection technology, a corneal thickness detection, technology, or a corneal curvature detection technology, but not limited to this.

Afterward, in step S16, the location determining unit automatically determines whether the eye detected by the detection unit is a left-eye or a right-eye.

In fact, the location determining unit can include a proximity sensor. When the detection unit approaches the eye of the person to be tested, the proximity sensor automatically senses whether the detection unit moves left or right to determine the eye detected by the detection unit is the left-eye or the right-eye. The proximity sensor can be a capacitive-resistive type, a photoelectric emitting-receiving type, a flux induction type, an ultrasound type, or an optical scale type.

In addition, of the optical apparatus is hand-held, and the location determining unit includes a motion sensor. When the optical apparatus is held by a hand to approach the eye of the person to be tested, the motion sensor automatically senses whether the hand moves left or right to determine the eye detected by the detection unit is the left-eye or the right-eye.

Finally, in step S18, the data output unit selectively outputs a detection result of the detection unit, a comparing result of the data comparing unit, and/or a determining result of the location determining unit. In practical applications, the data output unit can mark the detection result of the detection unit, the comparing result of the data comparing unit, and/or the determining result of the location determining unit by displaying graphic data or text data.

Compared to the prior arts, the optical apparatus and the operating method thereof have many advantages as follows.

(1) capable of automatically identifying the person to be tested;

(2) capable of cooperating with other optical detection apparatus with different functions, such as an optometry machine, a tonometer, a fundus camera, a corneal thickness meter, and an optical coherence tomography (OCT);

(3) capable of rapidly determining whether the eye detection data is related to left-eye or right-eye;

(4) capable of providing the tracking and comparing result of the detection data.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical apparatus, applied to ophthalmology detection, the optical apparatus comprising:
    an image capturing unit, for capturing images of different portions of a face of a person to be tested to obtain a plurality of face images;
    a data comparing unit, coupled to the image capturing unit, for comparing the plurality of face images with a built-in database;
    a detection unit, coupled to the data comparing unit, for detecting on an eye of the person to be tested;
    a location determining unit, coupled to the data comparing unit, for automatically determining whether the eye detected by the detection unit is a left-eye or a right-eye; and
    a data output unit, coupled to the data comparing unit, for selectively outputting a detection result of the detection unit, a comparing result of the data comparing unit, and/or a determining result of the location determining unit.

2. The optical apparatus of claim 1, wherein the data comparing unit compares the plurality of face images with the built-in database to determine whether the person to be tested is a new tester.

3. The optical apparatus of claim 1, wherein the location determining unit comprises a proximity sensor, when the detection unit approaches the eye of the person to be tested, the proximity sensor automatically senses whether the detection unit moves left or right to determine the eye detected by the detection unit is the left-eye or the right-eye.

4. The optical apparatus of claim 3, wherein the proximity sensor is a capacitive-resistive type, a photoelectric emitting-receiving type, a flux induction type, an ultrasound type, or an optical scale type.

5. The optical apparatus of claim 1, wherein the optical apparatus is hand-held, the location determining unit comprises a motion sensor, when the optical apparatus is held by a hand to approach the eye of the person to be tested, the motion sensor automatically senses whether the hand moves left or right to determine the eye detected by the detection unit is the left-eye or the right-eye.

6. The optical apparatus of claim 1, wherein the detection unit detects on the eye of the person to be tested via an optometry technology, a fundus photography technology, an optical coherence tomography (OCT) technology, an intraocular pressure (TOP) detection technology, a corneal thickness detection technology, or a corneal curvature detection technology.

7. The optical apparatus of claim 1, wherein the data output unit marks the detection result of the detection unit, the comparing result of the data comparing unit, and/or the determining result of the location determining unit by displaying graphic data or text data.

8. A method of operating an optical apparatus, applied to ophthalmology detection, the optical apparatus comprising an image capturing unit, a data comparing unit, a detection unit, a location determining unit, and a data output unit, the method comprising steps of:
   (a) the image capturing unit capturing images of different portions of a face of a person to be tested to obtain a plurality of face images;
   (b) the data comparing unit comparing the plurality of face images with a built-in database;
   (c) the detection unit detecting on an eye of the person to be tested;
   (d) the location determining unit automatically determining whether the eye detected by the detection unit is a left-eye or a right-eye; and
   (e) the data output unit selectively outputting a detection result of the detection unit, a comparing result of the data comparing unit, and/or a determining result of the location determining unit.

9. The method of claim 8, wherein in step (b), the data comparing unit compares the plurality of face images with the built-in database to determine whether the person to be tested is a new tester.

10. The method of claim 8, wherein in step (d), the location determining unit comprises a proximity sensor, when the detection unit approaches the eye of the person to be tested, the proximity sensor automatically senses whether the detection unit moves left or right to determine the eye detected by the detection unit is the left-eye or the right-eye.

11. The method of claim 10, wherein the proximity sensor is a capacitive-resistive type, a photoelectric emitting-receiving type, a flux induction type, an ultrasound type, or an optical scale type.

12. The method of claim 11, wherein the optical apparatus is hand-held, the location determining unit comprises a motion sensor, in step (d), when the optical apparatus is held by a hand to approach the eye of the person to be tested, the motion sensor automatically senses whether the hand moves left or right to determine the eye detected by the detection unit is the left-eye or the right-eye.

13. The method of claim 8, wherein in step (c), the detection unit detects on the eye of the person to be tested via an optometry technology, a fundus photography technology, an optical coherence tomography (OCT) technology, an intraocular pressure (IOP) detection technology, a corneal thickness detection technology, or a corneal curvature detection technology.

14. The method of claim 8, wherein in step (e), the data output unit marks the detection result of the detection unit, the comparing result of the data comparing unit, and/or the determining result of the location determining unit by displaying graphic data or text data.

* * * * *